United States Patent
Yang et al.

(10) Patent No.: US 11,918,228 B2
(45) Date of Patent: Mar. 5, 2024

(54) LEFT ATRIAL APPENDAGE OCCLUDER

(71) Applicant: LIFETECH SCIENTIFIC (SHENZHEN) CO., LTD., Guangdong (CN)

(72) Inventors: Bing Yang, Shenzhen (CN); Anning Li, Shenzhen (CN); Shuo Shan, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 17/780,722

(22) PCT Filed: Nov. 25, 2020

(86) PCT No.: PCT/CN2020/131516
§ 371 (c)(1),
(2) Date: May 18, 2023

(87) PCT Pub. No.: WO2021/115125
PCT Pub. Date: Jun. 17, 2021

(65) Prior Publication Data
US 2023/0285029 A1    Sep. 14, 2023

(30) Foreign Application Priority Data
Dec. 11, 2019    (CN) .......................... 201911268544.5

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12168* (2013.01); *A61B 17/12031* (2013.01)

(58) Field of Classification Search
CPC ........ A61B 17/12122; A61B 17/12172; A61B 2017/00893; A61B 17/12031;
(Continued)

(56) References Cited

U.S. PATENT DOCUMENTS

| 2003/0069606 A1 | 4/2003 | Girouard et al. |
| 2021/0369283 A1* | 12/2021 | O'Halloran ...... A61B 17/12172 |

FOREIGN PATENT DOCUMENTS

| CN | 203736560 U | 7/2014 |
| CN | 105708544 A | 6/2016 |

(Continued)

OTHER PUBLICATIONS

Notification to Grant Patent dated Oct. 25, 2022, in corresponding Chinese Application No. 201911268544.5, 3 pages.
(Continued)

*Primary Examiner* — Jon Eric C Morales
(74) *Attorney, Agent, or Firm* — Maier & Maier, PLLC (57) ABSTRACT

A left atrial appendage (LAA) occluder includes a sealing portion and a fixing portion connected to the sealing portion, and one or more sealed seed sources encapsulated with radioactive particles. The sealed seed sources are arranged on the sealing portion and/or the fixing portion (20) and configured for forming an annular isolation band on an inner wall of an LAA after the radioactive particles are released. The annular isolation band is configured for blocking the electrical signal conduction between the LAA and a left atrium. In the LAA occluder, the annular isolation band is formed on the inner wall of the LAA by the release of the radioactive particles in the sealed seed sources arranged on the sealing portion and/or the fixing portion.

11 Claims, 6 Drawing Sheets

(58) Field of Classification Search
CPC .......... A61B 2017/00035; A61B 2017/00084; A61B 2017/12095; A61B 2018/00351; A61B 2018/00613; A61B 2018/00839; A61B 2560/0219; A61N 2005/1004; A61N 2005/1011; A61N 5/1014
See application file for complete search history.

(56) References Cited

FOREIGN PATENT DOCUMENTS

| CN | 106659868 A | 5/2017 |
|----|-------------|--------|
| CN | 106994030 A | 8/2017 |
| CN | 108136203 A | 6/2018 |
| CN | 108525142 A | 9/2018 |
| CN | 207822261 U | 9/2018 |
| CN | 110215254 A | 9/2019 |

OTHER PUBLICATIONS

Second Office Action dated Jul. 5, 2022, in corresponding Chinese Application No. 201911268544.5, 35 pages.
First Office Action dated Oct. 9, 2021, in corresponding Chinese Application No. 201911268544.5, 34 pages.
International Search Report dated Mar. 3, 2021, in corresponding to International Application No. PCT/CN2020/131516; 6 pages (with English Translation).
First Office Action dated Oct. 9, 2021, corresponding to Chinese Application No. 201911268544.5; 15 pages (with English Translation).
Examination Report dated Nov. 24, 2022, in corresponding Indian Application No. 202217038346, 5 pages.
The Second Office Action dated Jul. 5, 2022, in corresponding Chinese Application No. 201911268544.5, 15 pages.

* cited by examiner

LEFT ATRIAL APPENDAGE OCCLUDER

TECHNICAL FIELD

The embodiments relate to the technical field of intervention medical instruments, and in particular, to a left atrial appendage (LAA) occluder.

BACKGROUND

Atrial fibrillation is the most common arrhythmia in clinical practice, with an incidence of 1.0%-1.5%, which increases with age. Atrial fibrillation may impair the cardiac function of patients and induce thrombosis, seriously affecting the quality of life. Atrial fibrillation is the strongest independent risk factor for stroke and heart failure, and 20% of stroke events are related to atrial fibrillation, which poses a great threat to the life safety of patients.

Atrial fibrillation is mainly caused by the disorder of electrical signals in heart. The pulmonary vein (vena cava) muscle sleeves and the special structures of atria such as ridge, coronary sinus and Marshall ligament may generate electrical activities spontaneously, which may drive or trigger an atrial electrical activity to cause atrial fibrillation accordingly. In 1997, Haissaguerre found that the electrical activity of the pulmonary vein muscle sleeves could drive/trigger the atrial electrical activity to cause atrial fibrillation and therefore proposed that isolation of an electrical connection between a pulmonary vein and a left atrium by radio frequency catheter ablation could terminate atrial fibrillation. Transcatheter ablation of atrial fibrillation has gone through the difficult exploration process of optimizing the surgical method. So far, it has been agreed that circumferential pulmonary vein ablation is the surgical cornerstone and the necessary ablation diameter can be increased as needed and the fragmentation potential and nerve plexus ablation can also be increased on this basis. However, conventional ablation usually has the disadvantages of long operation time, large ablation area and incomplete ablation, and cannot completely prevent current foldback, resulting in the possibility of recurrence of atrial fibrillation.

LAA is not only the main part of atrial fibrillation (AF) thrombosis, but also one of the key regions for its occurrence and maintenance due to the special morphology and structure thereof. Some patients with AF can benefit from an active left atrial appendage isolation (LAAI). In addition, aggressive ablation in the left atrium is often required for non-paroxysmal atrial fibrillation to reach an ablation endpoint, which is prone to a passive LAAI. Iatrogenic LAAI associated with ablation can theoretically increase the risk of thromboembolic events, which requires a high degree of vigilance by electrophysiologists.

However, it is difficult to perform the active LAAI, and the myocardium between pectinate muscles of the LAA is very thin, and during catheter ablation, it is possible that a gap between the pectinate muscles protrudes into a pericardial cavity, resulting in cardiac tamponade. And the position of the LAA is not convenient for catheter access, which makes the operation difficult.

SUMMARY

The embodiments provide an LAA occluder to solve the problems of high operational difficulty and high risk in implementing an active LAAI.

An LAA occluder includes a sealing portion and a fixing portion connected to the sealing portion. The LAA occluder further includes one or more sealed seed sources encapsulated with radioactive particles. The sealed seed sources are arranged on the sealing portion and/or the fixing portion and configured for forming an annular isolation band on an inner wall of an LAA after the radioactive particles are released. The annular isolation band is configured for blocking the electrical signal conduction between the LAA and a left atrium.

In one embodiment, the sealing portion or the fixing portion is provided with at least one flow blocking membrane on which the sealed seed sources are fixed.

In one embodiment, the sealed seed sources are evenly distributed near an edge of the flow blocking membrane.

In one embodiment, the fixing portion includes a plurality of supporting rods or woven wires, which are provided with the sealed seed sources respectively.

In one embodiment, at least one supporting rod is provided with a hole-groove structure in which the sealed seed sources are fixedly placed.

In one embodiment, the sealed seed sources are arranged at a proximal end of the fixing portion.

In one embodiment, the sealed seed sources are evenly distributed in a circumferential direction of the sealing portion or the fixing portion.

In one embodiment, vertical distances from the various sealed seed sources on the sealing portion or the fixing portion to a central axis of the LAA occluder are equal.

In one embodiment, the sealing portion includes a sealing disc and a balloon having an open end, a proximal end of the sealing disc is provided with a hollow proximal connector, the balloon is located inside the sealing disc, and the open end is sleeved at a distal end of the proximal connector.

In one embodiment, the sealed seed source is capable of being injected into the balloon through a catheter when the LAA occluder is unfolded, and the catheter is removably connected to the proximal connector.

According to the LAA occluder provided in the embodiments, the annular isolation band is formed on the inner wall of the LAA by the release of the radioactive particles in the sealed seed sources arranged on the sealing portion and/or the fixing portion, so as to block the electrical signal conduction between the LAA and the left atrium, thereby realizing the electrical isolation between the LAA and the left atrium. Therefore, patients can enjoy the benefits of long-term maintenance of sinus rhythm after the electrical isolation between the LAA and the left atrium, thereby reducing the probability of thrombus formation at the LAA, avoiding the operational difficulty and risk of the active left atrial appendage isolation (LAAI), and also achieving the occlusion of the LAA. Under the dual role of electrical isolation and occlusion, the occurrence of stroke can be better prevented, and the postoperative treatment effect is better.

DETAILED DESCRIPTION OF THE EMBODIMENTS

In order to facilitate the understanding of the embodiments, the embodiments will be described more comprehensively below with reference to relevant drawings. Implementations of the embodiments are given in the drawings. However, the embodiments may be implemented in many different forms, and are not limited to the implementations described herein. Conversely, these implementations are provided so that the embodiments herein are understood more thoroughly and comprehensively.

It should be noted that when an element is referred to as being "fixed" or "arranged" to another element, it may be directly on another element or centered elements may also be present. When an element is referred to as being "connected" to another element, it may be directly connected to another element or centered elements may also be present. The terms "vertical", "horizontal", "left", "right" and the like as used herein are for illustrative purposes only and are not meant to be the only implementations.

Unless defined otherwise, all technical and scientific terms used herein have the same meaning as commonly understood by those skilled in the art to which the embodiments belong. The terms used in the description of the embodiments herein are for the purpose of describing specific implementations only and are not intended to be limiting of the embodiments. The term "and/or" as used herein includes any and all combinations of one or more of the associated listed items.

In the field of interventional medical instruments, an end of a medical instrument implanted in a human or animal body that is closer to an operator is generally referred to as a "proximal end", an end that is further away from the operator is referred to as a "distal end", and the "proximal end" and "distal end" of any component of the medical instrument are defined in accordance with this principle. A position where a left atrium enters an LAA is defined as an ostium of the LAA and a position in the LAA adjacent to an entrance to the LAA is defined as a neck of the LAA. An "axial direction" generally refers to a longitudinal direction of the medical instrument when being delivered, and a "radial direction" generally refers to a direction of the medical instrument perpendicular to the "axial direction" thereof, and the "axial direction" and "radial direction" of any component of the medical instrument are defined in accordance with this principle.

Most of LAA occluders adopt the structures of filling in the LAA and sealing the ostium of the LAA, including a plug structure and a double-disc structure. Hereinafter, various embodiments will be described by taking a split-type double-disc structure as an example. It will be understood that in an integrally formed LAA occluder, a portion for occlusion may be regarded as a sealing portion in the embodiments and a portion for fixing the LAA occluder may be regarded as a fixing portion in the embodiments. Thus, the LAA occluder of the embodiments includes both split and integrally formed structures.

Figure 1:
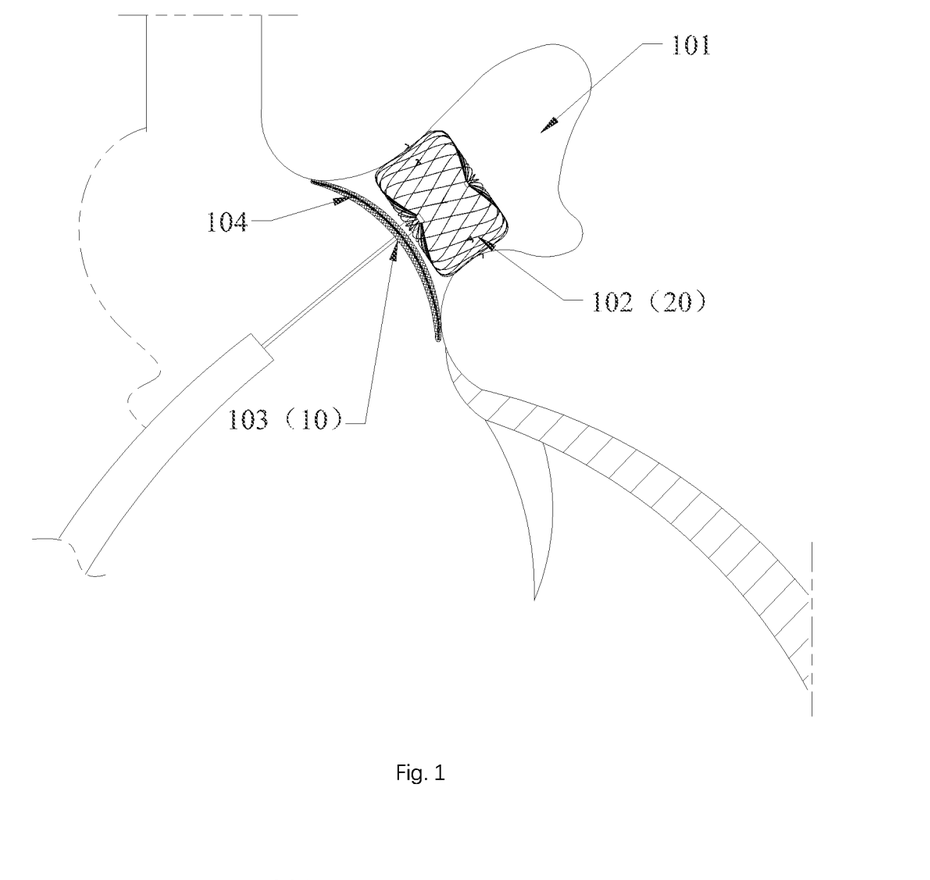
FIG. 1 is a schematic diagram of an LAA occluder implanted in an LAA position according to an embodiment.

FIG. 1 shows a schematic diagram of an LAA occluder implanted in an LAA 101 according to an embodiment. The LAA occluder includes a sealing portion 10 and a fixing portion 20 connected to the sealing portion 10. When the LAA occluder is implanted in the LAA 101, the fixing portion 20 is located in a cavity of the LAA 101 and closely attached to an inner wall of the LAA 101 to prevent the LAA occluder from falling out of the LAA 101. The sealing portion 10 is occluded at an ostium of the LAA 101 to prevent thrombus formed in the cavity of the LAA 101 from flowing into a left atrium and prevent blood flow from flowing from the left atrium to the cavity of the LAA 101.

The sealing portion 10 may have a disc-like, columnar or plug-like structure. For example, as shown in conjunction with FIG. 1, the sealing portion 10 is a sealing disc 103, and accordingly, the fixing portion 20 may be a fixing disc 102 connected to the sealing disc 103. The sealing portion 10 and the fixing portion 20 may be connected directly or through an intermediate member.

At least one layer of flow blocking membrane 104 is arranged inside or on a disc surface of the sealing disc 103, and is configured for preventing the circulation of blood from the left atrium to the LAA to ensure that the ostium of the LAA is tightly occluded.

Further, at least one flow blocking membrane (not shown) may be arranged inside or outside the fixing disc 102, so as to achieve multiple occlusion in cooperation with the sealing disc 103, thereby improving the occlusion performance for the LAA.

In an embodiment in which the sealing portion 10 is the sealing disc 103, the size of the flow blocking membrane 104 on the sealing disc 103 is equivalent to the size of the disc surface of the sealing disc 103, so that the flow blocking membrane 104 can completely cover the disc surface of the sealing disc 103 to achieve tight occlusion. For example, when the flow blocking membrane 102 and the sealing disc 103 are both regular circular, the diameter of the flow blocking membrane 104 is equal to or less different from the diameter of the sealing disc 103.

The flow blocking membrane 104 is a polymeric material, for example poly tetra fluoroethylene (PTFE) or polyethylene terephthalate (PET). The flow blocking membrane 104 may be fixed on a metal wire of the sealing disc 103 by suturing or bonding.

The LAA occluder according to the embodiments carries sealed seed sources encapsulated with radioactive particles, so that after the LAA occluder is implanted into the LAA 101, the radioactive particles are released to radiate a part of myocardial cells in the cavity of the LAA 101 and cause necrosis to the part of myocardial cells. Moreover, since the sealed seed sources are arranged on the LAA occluder, an annular isolation band can be formed on the inner wall of the LAA 101 to block the electrical signal conduction between the LAA 101 and the left atrium, thereby achieving the effect of electrical isolation, so that patients enjoy the benefits of long-term maintenance of sinus rhythm after the electrical isolation between the LAA 101 and the left atrium. In addition, after being released in the LAA 101, the LAA occluder can be firmly fixed in the LAA 101 and can occlude the ostium of the LAA 101, so as to realize the electrical isolation between the LAA 101 and the left atrium while realizing the occlusion of the LAA 101, thereby preventing patients from having a stroke by double guarantee. In addition, on the one hand, the electrical isolation between the LAA 101 and the left atrium terminates the abnormal conduction of electrical signals near the LAA 101, which is beneficial to improving the postoperative quality of life of patients, for example, the alleviation of atrial fibrillation symptoms and other discomfort symptoms and the reduction of patients' pain; on the other hand, after the LAA 101 is electrically isolated from the left atrium, the amplitude of contraction or relaxation of the LAA will be smaller than before, so that the influence on the LAA occluder implanted in the LAA 101 is relatively small, which is beneficial to the stability of the LAA occluder fixed in the LAA 101.

It should be noted that the annular isolation band referred to in the embodiments may have a continuous annular shape without gaps or may have a generally annular shape. For example, the annular isolation band has a generally annular shape, there are only a plurality of small gaps in the annular shape, abnormal electrical signals from the LAA 101 to the left atrium through these gaps are relatively weak, and the influence of these abnormal electrical signals on conduction-induced thrombosis is substantially negligible.

The sealed seed sources may be arranged on the sealing portion 10 of the LAA occluder or may be arranged on the fixing portion 20 of the LAA occluder. In other embodiments, the sealing portion 10 and the fixing portion 20 are both provided with sealed seed sources, the specific positions of the sealed seed sources are not limited herein, and it is only necessary that the radioactive particles released by the sealed seed sources can form an annular isolation band on the inner wall of the LAA 101 so as to block the electrical signal conduction between the LAA 101 and the left atrium.

Further, the sealed seed sources are evenly distributed in a circumferential direction of the sealing portion 10 or the fixing portion 20, so as to avoid uneven distribution of radiation caused by uneven distribution of the sealed seed sources, and the influence on an electrical isolation effect between the LAA 101 and the left atrium.

Vertical distances from the various sealed seed sources on the sealing portion 10 or the fixing portion 20 to a central axis of the LAA occluder are equal. Thus, after the LAA occluder is released in the LAA 101, the fixing portion 20 is fixed with the inner wall of the LAA 101. At this time, the positions of the various sealed seed sources on the sealing portion 10 or the fixing portion 20 relative to the inner wall of the LAA 101 are basically consistent, so as to avoid the influence on the electrical isolation effect between the LAA 101 and the left atrium due to too large or small local radiation of the inner wall of the LAA 101.

In an embodiment in which the sealing portion 10 and/or the fixing portion 20 is provided with the flow blocking membrane, the sealed seed sources may be fixed on the flow blocking membrane and fixed to the sealing portion 10 and/or the fixing portion 20 with the flow blocking membrane. The material of the flow blocking membrane is relatively soft, so that the sealed seed sources can be fixed on the flow blocking membrane without falling off. On the other hand, the shape of the flow blocking membrane is often relatively regular, which is beneficial to the even distribution of the sealed seed sources on the flow blocking membrane, so as to ensure that the radioactive particles in the sealed seed sources can radiate the inner wall of the LAA 101 in an annular shape with the same amplitude.

In some embodiments, the sealed seed sources are arranged at a proximal end of the fixing portion 20, and the proximal end of the fixing portion 20 is not an end closest to the sealing portion 10 along its axis, but refers to a portion of the circumferential side of the fixing portion 20 close to the sealing portion 10. For convenience of understanding, the situation that the sealed seed sources are arranged at the proximal end of the fixing portion 20 is illustrated below only with an example in which the fixing portion 20 is in the shape of a mesh column shown in FIG. 1. The proximal end of the fixing portion 20 refers to a portion on the circumferential side of the mesh column close to the sealing portion 10 in an axial direction of the fixing portion 20. Accordingly, in the case where the fixing portion 20 has a non-mesh column structure, a central portion of the proximal end of the fixing portion 20 is connected to the sealing portion 10, and a portion of the circumferential side of the fixing portion 20 close to the sealing portion 10 is defined as the proximal end of the fixing portion 20. Thus, after the LAA occluder is released in the LAA 101, the circumferential side of the fixing portion 20 is fixed to the inner wall of the LAA 101, so that the sealed seed sources arranged at the proximal end of the fixing portion 20 will be as close to the ostium or neck of the LAA 101 as possible. The radiation influence of the sealed seed sources on the tissue at the LAA 101 is thereby reduced, and it is ensured that the formed annular isolation band reliably blocks the electrical signal conduction between the LAA 101 and the left atrium.

Hereinafter, the formation of the annular isolation band near the ostium of the LAA 101 will be described as an example.

Figure 2:
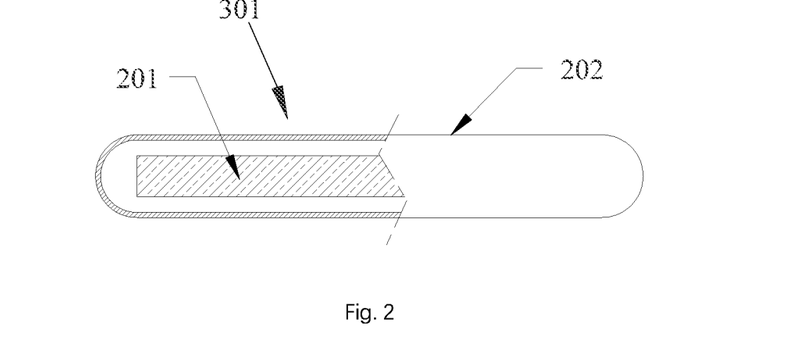
FIG. 2 is a schematic structure diagram of a sealed seed source containing radioactive particles configured for an LAA occluder according to an embodiment.

FIG. 2 schematically shows one embodiment of a basic structure of a sealed seed source 301 with radioactive particles carried by an LAA occluder of the embodiments.

As shown in FIG. 2, the sealed seed source 301 with radioactive particles includes an inner core 201 and a housing 202. The inner core 201 is not limited in shape, which may be a sphere, a column, a rod, etc. Most materials are high atomic number metals (silver, calcium, pincers, etc.), ceramics, ion exchange resins, glass spheres coated with silver, etc.

The inner core 201 is configured for loading a certain quantity of radioactive particles. There are two main methods for loading radioactive particles. In the first method, the radioactive particles are immersed inside the inner core 201. In this way, the radioactive particles may be randomly distributed in various positions of the inner core 201. In the second method, the radioactive particles are plated on the surface of the inner core 201. In this way, the radioactive particles are randomly distributed on the surface of the inner core 201.

The housing 202 of the sealed seed source 301 is made of a titanium tube. Titanium has the characteristics of high mechanical strength, small absorption of radiation, good chemical stability, strong corrosion resistance, good cold and thermal stability, etc., is non-toxic and harmless, and has a density similar to human bones, is easily contained by a human body, and has good biocompatibility. Radioactive elements will not leak out from the housing 202. Optional radioactive particles for the sealed seed source 301 include, but are not limited to, iodine-125 (I-125), palladium-103 (Pd-103), iridium-192 (Ir-192), etc. Such elements are characterized by a short half-life period, a short radiation distance, and a small influence on tissues other than an implantation position, so that such elements can be configured for radiating a designated position of the inner wall of the LAA 101. Taking myocardial cells near the ostium of the LAA 101 as an example, the myocardial cells near the ostium of the LAA 101 may be necrotized, thereby achieving the effect of the electrical isolation between the LAA 101 and the left atrium, and less damage to other tissues in the body.

It should be noted that the principle of the electrical isolation between the LAA 101 and the left atrium by the radioactive particles is to use rays released by the radioactive particles to cause single-strand breakage or double-strand breakage of biological macromolecules such as DNA and RNA in the cells, thereby affecting the viability of the cells. Meanwhile, the radioactive particles react with cytosol or cytoplasm to generate free radicals and/or oxides, resulting in cell damage.

The LAA occluder carrying radioactive particles in this embodiment has the characteristics that the radioactive particles inside have a small radiation range and a large radiation intensity in a local radiation range. The radiation intensity and the radiation range may be adjusted by the selection and dosage of radioactive elements and the arrangement position on the LAA occluder, etc.

Embodiment 1

An LAA occluder provided in Embodiment 1 may be in the form of a plug structure or a double-disc structure. As to the structural form of the LAA occluder, there is no limitation here, and for the convenience of description, the LAA occluder in the form of a double-disc structure will be taken as an example below.

Figure 3:
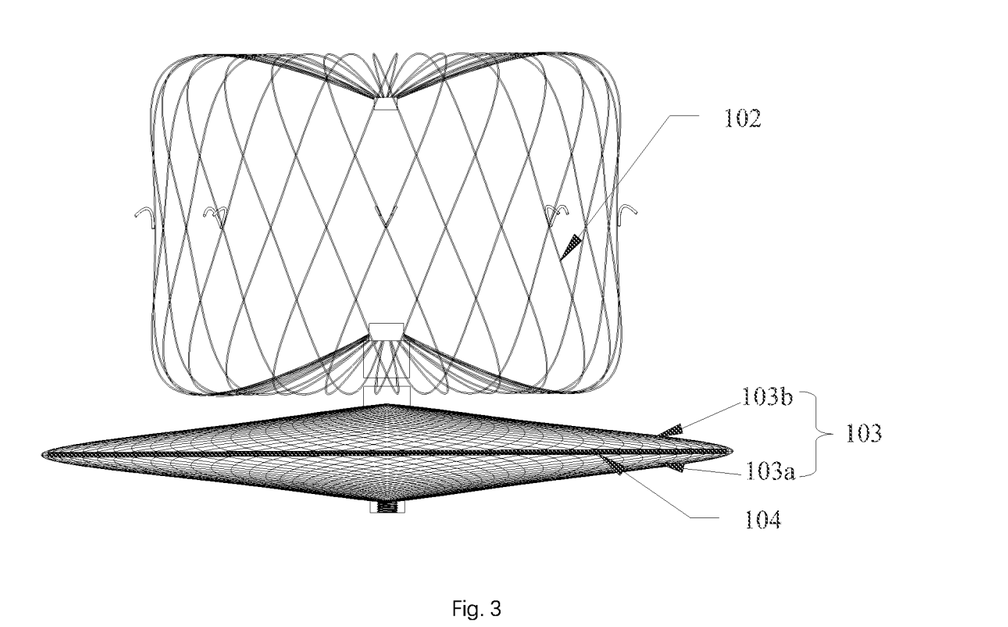
FIG. 3 is a schematic structure diagram of an LAA occluder according to an embodiment.
Figure 4:
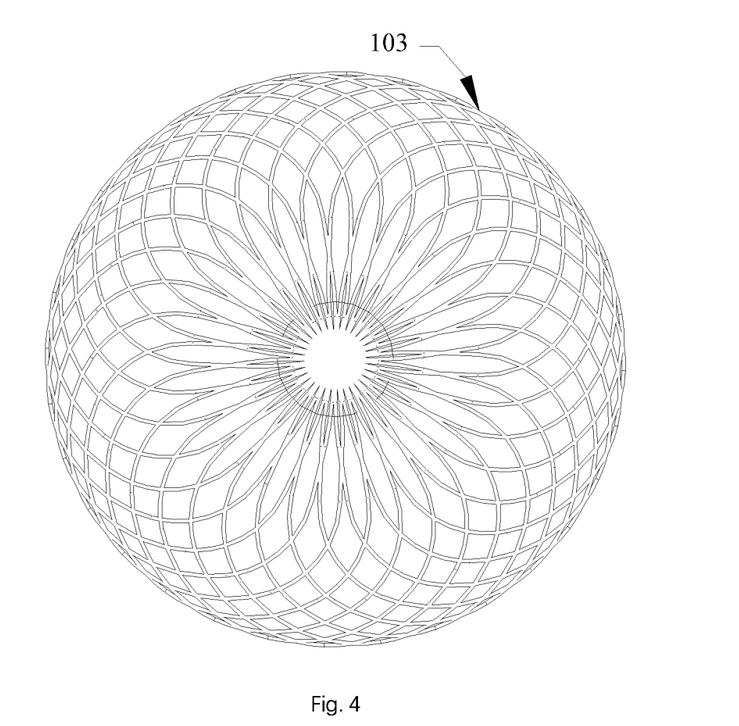
FIG. 4 is a schematic bottom view of a sealing disc of the LAA occluder in Embodiment 1.

As shown in conjunction with FIGS. 3 and 4, the LAA occluder includes a fixing disc 102 and a sealing disc 103. The sealing disc 103 is formed into a disc-shaped structure by heat treatment using a woven mesh tube structure. A flow blocking membrane 104 is arranged in the sealing disc 103, and an edge of the flow blocking membrane 104 is fixed on a woven wire at an edge of the sealing disc 103 by suturing or bonding, etc. The manner in which the flow blocking membrane 104 is fixed to the sealing disc 103 is not limited herein.

Figure 5:
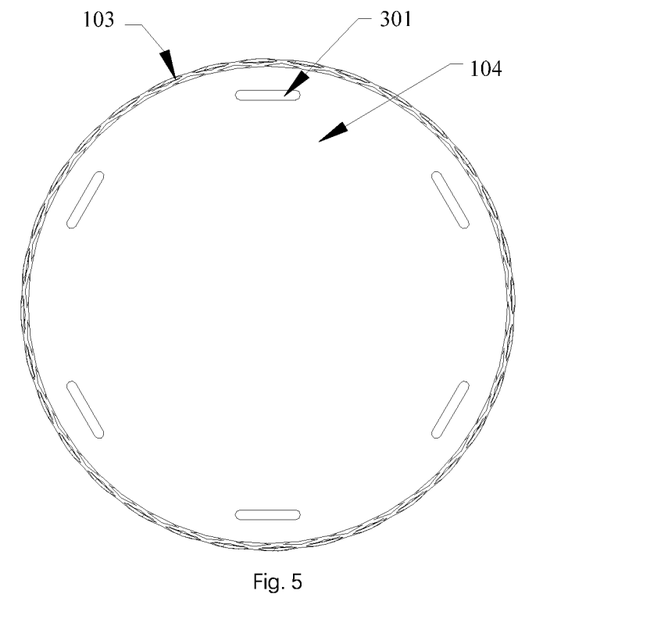
FIG. 5 is a schematic top view of the sealing disc of the LAA occluder shown in FIG. 4 covered with a flow blocking membrane, in which the arrangement of sealed seed sources is schematically shown.

As shown in conjunction with FIG. 5, a sealed seed source 301 encapsulated with radioactive particles is fixed on the flow blocking membrane 104. The manner in which the sealed seed source 301 is fixed on the flow blocking membrane 104 may be glue bonding, suturing after the flow blocking membrane 104 wraps the sealed seed source 301, etc., and will not be limited herein. In other embodiments, the sealed seed source 301 may also be fixed on a proximal disc surface 103a and/or a distal disc surface 103b of the sealing disc 103. For example, the sealed seed source 301 provided with a through hole is fixed on a woven wire of the proximal disc surface 103a and/or the distal disc surface 103b of the sealing disc 103 with a suture. The distribution manner of the sealed seed sources 301 on the flow blocking membrane 104 may take the form of even distribution, so as to avoid the uneven distribution of radiation caused by the uneven distribution of the sealed seed sources 301.

As shown in FIG. 5, the sealed seed sources 301 are evenly distributed near the edge of the flow blocking membrane 104, that is, the sealed seed sources 301 are equally spaced in the circumferential direction of the sealing disc 103. The spacing is determined according to the irradiation range of the radioactive particles in the sealed seed sources 301. Since an edge portion of the flow blocking membrane 104 is closest to the inner wall of the LAA 101, the even arrangement of the sealed seed sources 301 near the edge of the flow blocking membrane 101 enables the use of as little sealed seed sources 301 as possible to have a sufficient radiation influence on the inner wall of the LAA 101 and also avoids the influence of the sealed seed sources 301 on other tissues in the body.

The selection and arrangement of the sealed seed sources 301 may be calculated based on the amount of radiation to achieve myocardial cell necrosis near the ostium of the LAA. For example, if the common I-125 sealed seed source 301 has an irradiation range of 17 mm, the spacing between two adjacent sealed seed sources 301 should be 10 mm.

In the structural form of the sealed seed sources 301 evenly distributed, while the flow blocking membrane 104 occludes the ostium of the LAA 101, the sealed seed source 301 near the edge of the flow blocking membrane 104 will cause necrosis to myocardial cells located in an annular region near the ostium of the LAA 101, thereby forming an annular isolation band near the ostium of the LAA 101 to achieve the effect of the electrical isolation between the LAA 101 and the left atrium.

In some embodiments, the sealed seed sources 301 are evenly distributed near the edge of the flow blocking membrane 104, so that the sealed seed sources 301 can be better attached to the ostium of the LAA 101, so as to better radiate the myocardial cells near the ostium of the LAA 101. Meanwhile, even radiation is presented at the ostium of the LAA 101, so as to avoid the situation of uneven distribution of radiation due to the excessive irradiation overlapping range of some sealed seed sources 301 when the sealed seed sources 301 are unevenly distributed, which may not achieve the desired electrical isolation effect. Under this even radiation, the negative effect on tissues near the ostium of the LAA 101 caused by too much local radiation is also avoided.

It should be noted that in an embodiment in which the fixing portion 20 is provided with a flow blocking membrane, the sealed seed sources 301 may also be evenly distributed on the flow blocking membrane of the fixing portion 20, for example, at a position near the edge of the flow blocking membrane, or any annular region of the flow blocking membrane near the sealing portion 10.

It should be noted that the above-described "even distribution of the sealed seed sources 301" may allow a small amount of deviation. By controlling the amount of radioactive particles in the sealed seed sources 301 or the number of sealed seed sources 301 at the same position, the irradiation range of the sealed seed sources 301 at the same position may be controlled.

Figure 6:
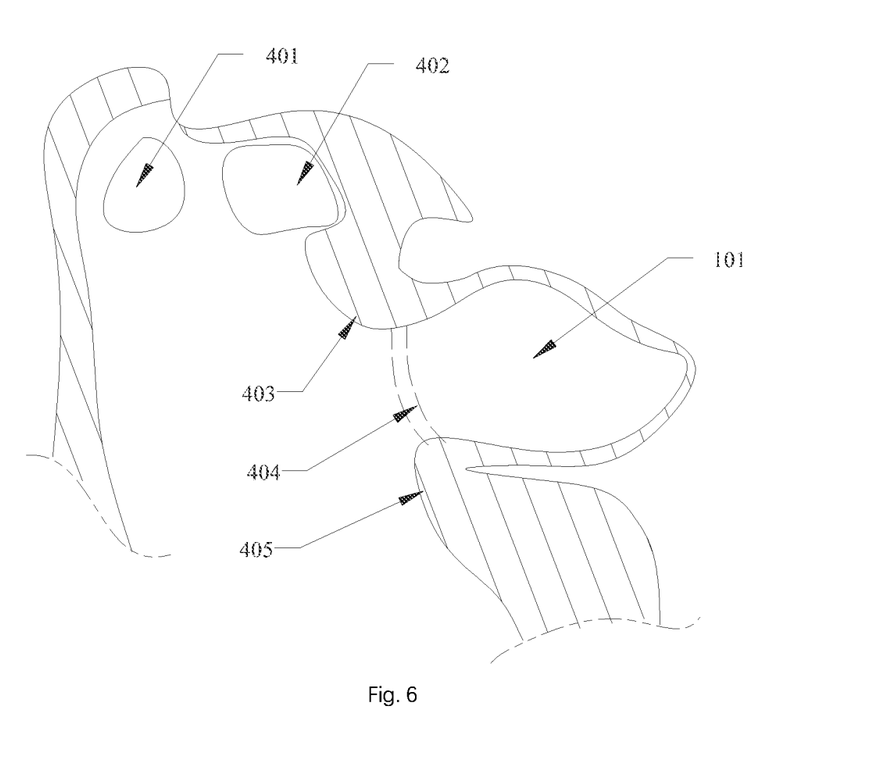
FIG. 6 shows main structures adjacent to an LAA electrically associated with atrial arrhythmias, in which a region shown in dashed lines is a position range of left atrial isthmus.

FIG. 6 schematically shows main structures adjacent to an LAA 101 electrically associated with atrial arrhythmias. In the embodiment, the main structures adjacent to the LAA 101 include: a left inferior pulmonary vein 401, a left superior pulmonary vein 402, a left superior pulmonary vein crest 403, a left atrial isthmus 404 (a region shown in dashed lines in FIG. 6, actually a part of tissues forming the ostium of the LAA 101), and a mitral isthmus 405.

Figure 7:
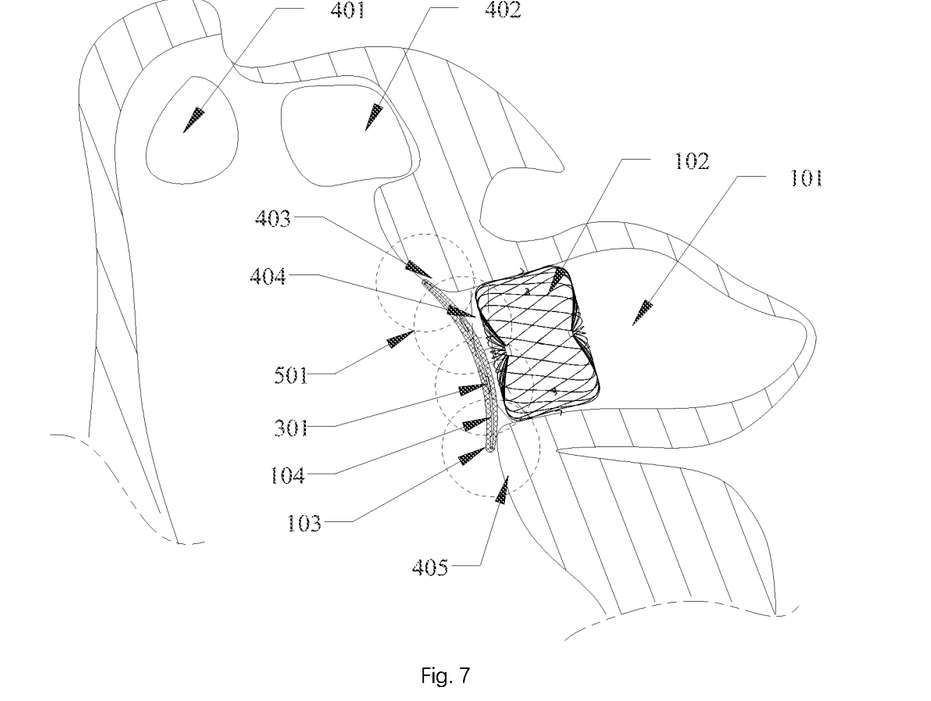
FIG. 7 is a schematic diagram of a radiation range of the sealed seed sources on the flow blocking membrane of the LAA occluder when the LAA occluder in Embodiment 1 is implanted into the LAA shown in FIG. 6.

As shown in conjunction with FIG. 7, a dashed circle portion 501 in FIG. 7 schematically shows a radiation region of each sealed seed source 301. It can be seen from FIG. 7 that the radiation regions of the plurality of sealed seed sources 301 arranged on the LAA occluder may have overlapping regions with each other, and the amount of radiation generated under the overlapping regions is relatively large.

Upon release of the LAA occluder, the flow blocking membrane 104, as a part of the sealing disc 103, is fully unfolded and occludes the ostium of the LAA 101. The cells at the ostium of the LAA 101 are within the radiation range of the sealed seed sources 301 with the radioactive particles carried by the LAA occluder.

For example, the left superior pulmonary vein crest 403, the left atrial isthmus 404, the mitral isthmus 405, a part of the left inferior pulmonary vein 401, and a part of the left superior pulmonary vein 402 are all within the irradiation range of the radioactive particles. The sealed seed sources 301 irradiate and necrotize the myocardial cells within its radiation range to form an annular isolation band near the ostium of the LAA 101 that interrupts the electrical signal conduction between the LAA 101 and the left atrium. As a result, the electrical isolation near the ostium of the LAA 101 is realized by using the sealed seed sources 301 arranged on the flow blocking membrane 104 while the flow blocking membrane 104 completes the occlusion of the ostium of the LAA 101.

It should be noted that the sealed seed source 301 on the LAA occluder may be arranged on any cross section of the LAA occluder in an axial direction thereof, generally, from the proximal end of the LAA occluder to the vicinity of a part where the fixing disc 102 contacts the inner wall of the LAA 101. For example, the sealed seed sources 301 may be arranged in the proximal or middle section of the fixing disc 102, or in the portion of the sealing disc 103 near its edge, so long as the sealed seed sources 301 are capable of irradiating myocardial cells within its radiation range and necrotizing the myocardial cells, thereby interrupting the electrical signal conduction from this position to the left atrium with less damage to other tissues.

Embodiment 2

The same or similar content of an LAA occluder in Embodiment 2 to the LAA occluder in Embodiment 1 will not be described in detail herein. A difference therebetween is that, as shown in conjunction with FIG. 8, the fixing disc 102 adopts a mesh rod structure including a plurality of supporting rods 601. For example, the fixing disc 102 includes two or more supporting rods 601.

In some embodiments, the plurality of supporting rods 601 of the fixing disc 102 are shaped by heat treatment after cutting a nickel-titanium tube. For example, as shown in conjunction with FIGS. 8 and 9, the plurality of supporting rods 601 of the fixing disc 102 are radially folded outwards. The supporting rod 601 has a fixed end 601*a* connected to the distal end of the sealing portion 10, and an overhanging section 601*b* connected to the fixed end 601*a*. An end of the overhanging section 601*b* away from the fixed end 601*a* radiates radially and is folded in an overhanging manner, and in an example, the overhanging section 601*b* of the supporting rod 601 is folded to the proximal end after extending towards the distal end for a certain length so as to have a substantially arch shape.

Figure 10:
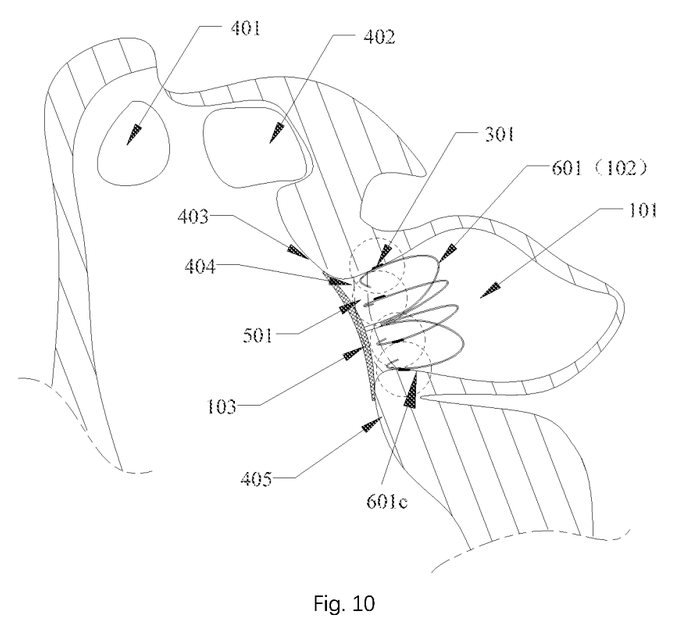
FIG. 10 is a schematic diagram of a radiation range of the sealed seed sources on the fixing disc of the LAA occluder when the LAA occluder in Embodiment 2 is implanted into the LAA shown in FIG. 6.

As shown in conjunction with FIG. 10, after the LAA occluder is placed in the LAA 101, since the fixing disc 102 is located in the cavity of the LAA 101, a part of a rod section of the supporting rod 601 folded towards the proximal end is in contact with the inner wall of the LAA 101 so as to integrally fix the LAA occluder in the cavity of the LAA 101, so that the sealing portion 10 is occluded at the ostium of the LAA 101, thereby preventing thrombus formed in the cavity of the LAA 101 from flowing into the left atrium, and preventing blood flow from flowing from the left atrium into the cavity of the LAA 101.

After implantation of the LAA occluder in the LAA 101, the proximal section of the supporting rod 601 is generally in contact with the myocardium of the LAA 101. In other embodiments, one or more of the supporting rods 601 may be provided with a hole-groove structure (not shown) that may be configured for fixedly placing the sealed seed sources 301 to ensure that the sealed seed sources 301 can be stably fixed on the fixing portion 20 without falling off. The hole-groove structure can be provided on the proximal section of the supporting rod 601.

The hole-groove structure may be a hole provided on the supporting rod 601 or may be a groove provided on the supporting rod 601. For example, a groove may be provided at an appropriate position on the supporting rod 601 to fix the sealed seed source 301 in the groove. The hole-groove structure of the supporting rod 601 may be formed by cutting away a part of the structure of the supporting rod 601.

It should be noted that the number and arrangement position of the supporting rods 601 may be set in accordance with the distribution of the sealed seed sources 301 and the device specifications. For the sealed seed sources 301 with different radioactive particles, due to different irradiation ranges, it is necessary to configure an appropriate spacing to appropriately radiate the myocardial cells at the ostium of the LAA 101 while avoiding adverse effects on other tissues. For example, taking the radioactive particles as iodine-125 particles as an example, the irradiation range of the sealed seed source 301 containing iodine-125 is about a circular region with a radius of 1.7 cm, and the arrangement spacing of the sealed seed source 301 may be controlled at 8-12 mm Therefore, the arrangement number and arrangement position of the supporting rods 601 need to be configured in coordination with the particle spacing required for the irradiation range of the sealed seed source 301 containing iodine-125.

In some embodiments, the supporting rod 601 has a rod width of 0.8-2.0 mm to provide suitable support strength, while allowing for a hole-groove structure for fixing radioactive particles.

In other embodiments, the manner in which the sealed seed source 301 is fixed on the supporting rod 601 is not limited to the hole-groove structure. For example, the sealed seed source 301 may be fixed on the supporting rod 601 by glue bonding, riveting, welding, or the like, without limitation herein.

Figure 8:
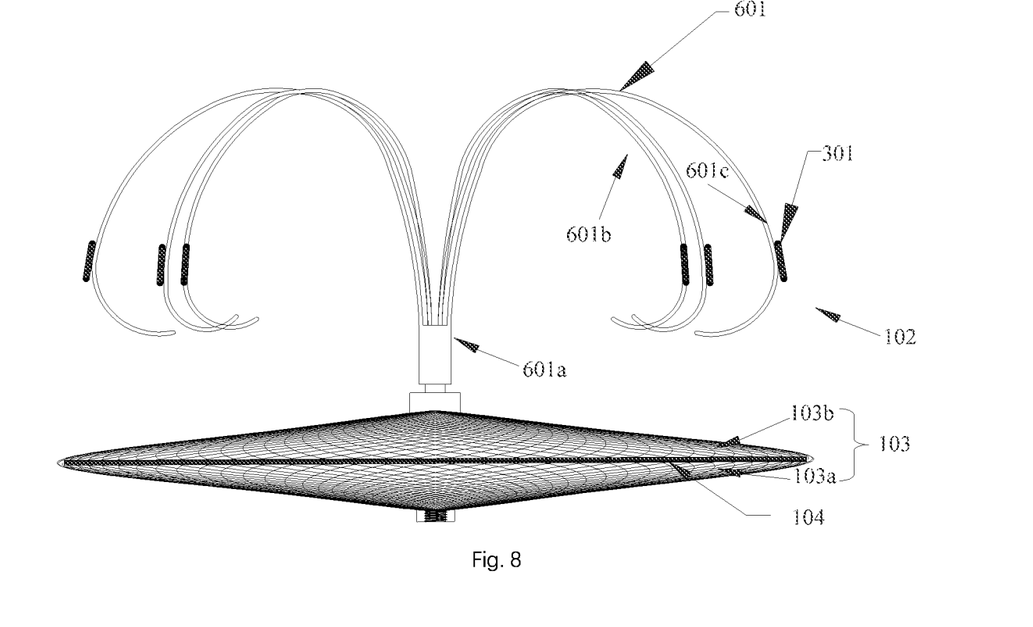
FIG. 8 is a schematic structure diagram of an LAA occluder in Embodiment 2, in which mounting positions of sealed seed sources on a fixing disc are schematically shown.
Figure 9:
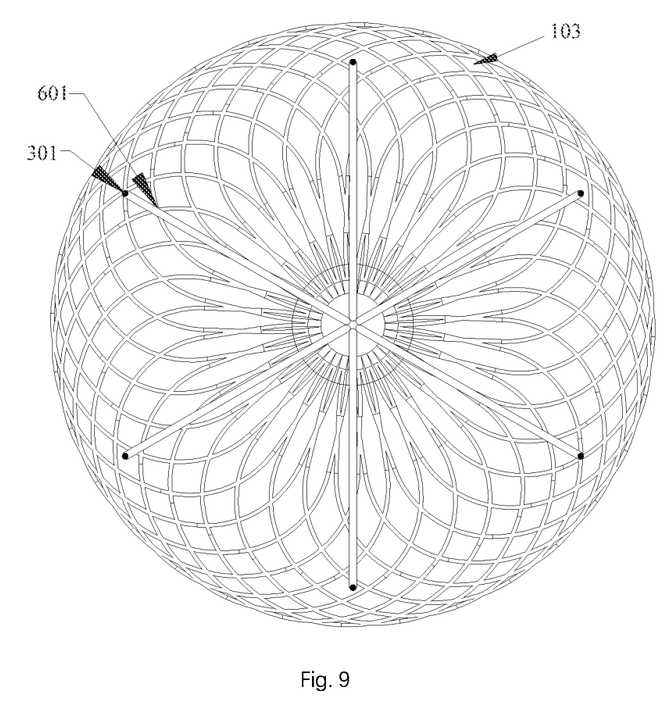
FIG. 9 is a schematic top view of the LAA occluder shown in FIG. 8.

As shown in conjunction with FIGS. 8-10, after the LAA occluder is unfolded, the sealed seed source 301 can be fixed at a corresponding location near the neck of the LAA 101 on the supporting rod 601, that is, a position adjacent to the ostium of the LAA 101 in the LAA 101. For example, as shown in conjunction with FIG. 8, the overhanging section 601*b* of the supporting rod 601 is folded to the proximal end after extending towards the distal end for a certain length, a portion of the overhanging section 601*b* which is folded towards the proximal end (hereinafter referred to as a "folded section 601*c*") is located on the periphery of the fixing disc 102, the sealed seed source 301 is fixed to the folded section 601*c*, namely, the sealed seed source 301 is located on the periphery of the fixing disc 102. Then after the LAA occluder is released in the LAA 101, referring to FIG. 10, the folded section 601*c* is in contact with the inner wall of the LAA 101, so that the sealed seed source 301 is close to the neck of the LAA 101, and the sealed seed source 301 radiates the myocardial cells near the neck of the LAA 101, thereby reducing the radiation influence of the sealed seed source 301 on other tissues in the LAA 101, and ensuring that the formed annular isolation band can reliably block the electrical signal conduction between the LAA 101 and the left atrium.

As shown in FIG. 10, after the LAA occluder is implanted, the fixing disc 102 is unfolded in the cavity of the LAA 101, and a part of the rod section of the supporting rod 601 thereof is adhered to the inner wall of the LAA 101, so that the sealed seed sources 301 attached on the supporting rod 601 can be arranged at or near the neck of the LAA 101, so that the neck of the LAA 101 is within the irradiation range, and the irradiation range of the sealed seed source 301 containing radioactive particles refers to the dashed circle portion region shown in FIG. 10.

The electrical conduction around the ostium of the LAA 101 is relatively complex, and the electrical conduction between the left atrium and a right atrium passes along a left branch of the Bachmann's bundle (interauricular bundle) at an anterior epicardial wall of the left atrium, and is divided, at a base portion of the LAA 101 (that is, the deepest part of the cavity of the LAA 101), into two bundles wrapping the LAA 101 and meeting at the inner wall of the LAA 101 at the epicardium. The septal pulmonary vein bundle and the septal atrial bundle of the endocardial surface are together shifted leftwards to wrap the front of the ostium of the LAA 101. The Marshall ligament is rich in nerve fibers and is connected to a coronary sinus rotator cuff or located on a free wall of the left atrium. A band-like anatomical isthmus is formed between the left superior pulmonary vein 402 and a mitral annulus as the mitral isthmus 405, and is located at the lower posterior side of the ostium of the LAA 101. Therefore, sites where the LAA 101 is connected to the left atrium are concentrated here.

After the LAA occluder is implanted, the radioactive particles in the sealed seed source 301 perform radioactive radiation, resulting in myocardial tissue necrosis within its irradiation range. An annular isolation band is formed on the inner wall of the LAA 101, thereby interrupting the electrical signal conduction from the LAA 101 to the left atrium and realizing the electrical isolation between the LAA 101 and the left atrium while completing the occlusion of the LAA 101.

In some embodiments, the fixing disc 102 is covered with at least one flow blocking membrane (not shown), and the sealed seed source 301 may also be fixed in place on the flow blocking membrane, for example corresponding to the proximal section of the fixing disc 102, that is, a portion of the circumferential side of the fixing disc 102 adjacent to the sealing disc 103. The sealed seed source 301 is wrapped with the flow blocking membrane and then sutured onto the fixing disc 102.

Embodiment 3

Figure 11:
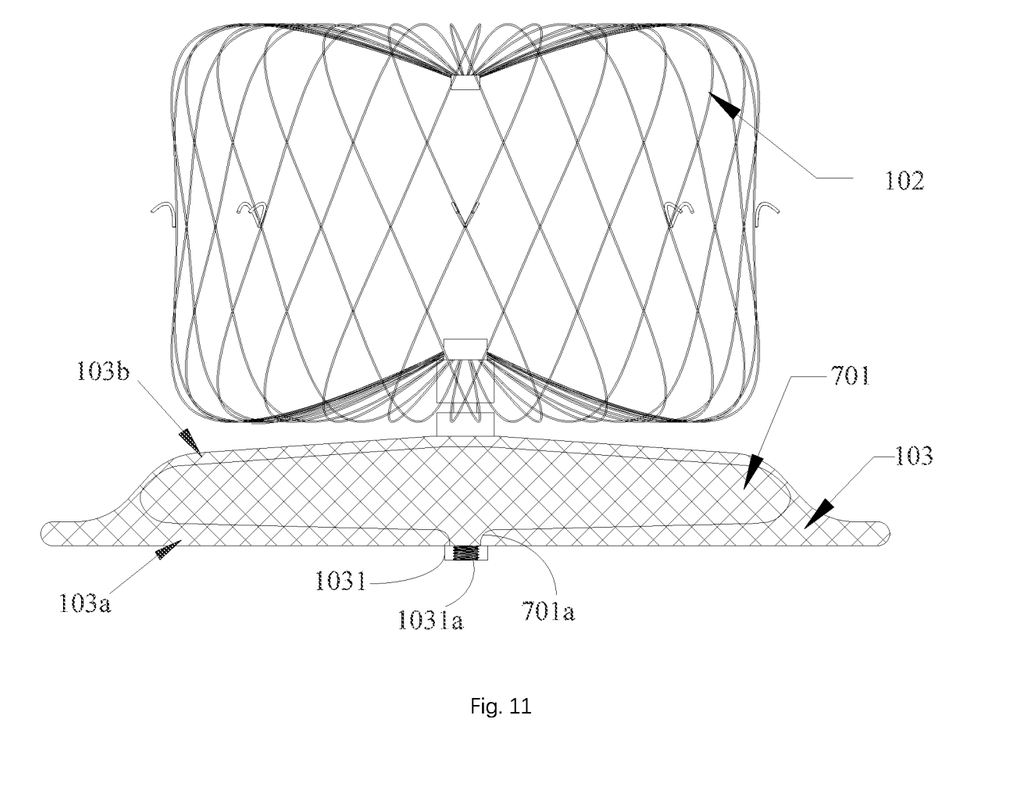
FIG. 11 is a schematic structure diagram of an LAA occluder in Embodiment 3, in which a balloon in a fixing disc is schematically shown.

As shown in conjunction with FIG. 11, in an LAA occluder of the present embodiment, as compared with Embodiment 1, a balloon 701 is arranged in the sealing disc 103.

The balloon 701 may be made of a compliant material, and the shape of the balloon may be changed accordingly according to the degree of inflation of the balloon 701, so as to match the traction of the fixing disc 102 on the sealing disc 103 and enhance the fitting degree between the sealing disc 103 and the ostium of the LAA 101, thereby improving the stability and occlusion performance of the LAA occluder.

In this embodiment, the radioactive particles may be encapsulated using microspheres, such as glass or ceramic microspheres, having a diameter of 15-155 μm. The radioactive particles encapsulated by the microspheres may be yttrium (Y-90) element, phosphorus-32 element, etc., and the half-life period of the two elements is short. The half-life period of yttrium is 2.7 days, and the half-life period of phosphorus is 14.3 days. The irradiation range of the sealed seed source 301 formed by encapsulating the two elements by the microspheres is small, which is suitable for the case where only a small amount of epidermal cells are irradiated at the ostium of the LAA 101.

It should be noted that, in the form of microsphere encapsulation in the present embodiment, the irradiation degree of myocardial cells can be controlled by increasing or decreasing the number of radioactive microspheres according to the size of the ostium of the LAA 101 and the wall thickness of the LAA 101 to be implanted.

As shown in FIG. 11, the proximal end of the sealing disc 103 is provided with a hollow proximal connector 1031. The balloon 701 is located inside the sealing disc 103 of the LAA occluder and is connected and fixed to the proximal connector 1031 in an unlimited manner, such as glue bonding or clamp connection.

In an example, the balloon 701 is a balloon-like structure having an open end 701*a*, and the open end 701*a* of the balloon 701 is sleeved on the proximal connector 1031. The proximal connector 1031 has a tube hole 1031*a* for inflating a substance into the balloon 701 from the tube hole 1031*a*. The tube hole 1031*a* of the proximal connector 1031 may be a threaded hole for delivery of the LAA occluder after connection with a pushing tube of a delivery device. In addition, an embolic agent containing radioactive microspheres and a contrast agent may be injected into the balloon 701 using the tube hole 1031*a* of the proximal connector 1031. The connection requirements of the pushing tube can be met, and the number of arranged tubes of the whole delivery device can also be reduced, so that the delivery device can meet the requirement of small tube diameter.

For convenience of further describing the structure of the LAA occluder, the surface of a side on which the proximal end of the sealing disc 103 is located is referred to as a "proximal disc surface 103*a*", and accordingly, the surface of a side on which the distal end of the sealing disc 103 is located is referred to as a "distal disc surface 103*b*".

With continued reference to FIG. 11, the proximal connector 1031 is fixed to the middle of the proximal disc surface 103*a*, and the balloon 701 is located between the proximal disc surface 103*a* and the distal disc surface 103*b* of the sealing disc 103. Because the open end 701*a* of the balloon 701 is sleeved on the proximal connector 1031, a catheter (not shown) for injecting the radioactive microspheres and the contrast agent, etc. into the balloon 701 may be connected to the proximal end of the proximal connector 1031 so that the catheter is communicated with the interior of the balloon 701 after being connected to the open end 701*a* of the balloon 701.

It should be noted that the catheter is detachably connected to the proximal connector 1031, so that the catheter is separated from the proximal connector 1031 after the LAA occluder is released. The specific manner in which the catheter is connected to the proximal connector 1031 is not limited. For example, the catheter is in threaded connection with the proximal connector 1031. In other implementations, the catheter may be connected to the proximal connector 1031 by a snap fit or transition fit connection.

Referring to FIGS. 3 and 8, when the flow blocking membrane 104 is arranged on the sealing disc 103, the flow blocking membrane 104 of the sealing disc 103 may be arranged between the proximal disc surface 103*a* and the distal disc surface 103*b*. In the present embodiment, the flow blocking membrane 104 is located between the balloon 701 and the distal disc surface 103*b* to ensure that the occlusion effect of the flow blocking membrane 104 is not disturbed by the balloon 701. In this embodiment, the flow blocking membrane 104 may be fixed on the distal disc surface 103*b* by suturing connection or glue bonding, which will not be described further herein.

After the LAA occluder is unfolded in the LAA 101, the embolic agent mixed with the radioactive microspheres and the contrast agent is injected into the balloon 701 through the catheter, and the height and radiation range of the balloon 701 in an axial direction are observed and controlled through imaging. Because the embolic agent is more viscous and the microspheres have less mass, the microspheres will not aggregate or migrate under the action of gravity. During filling of the embolic agent into the balloon 701, the microspheres encapsulating the radioactive particles are randomly and more evenly distributed in the balloon 701.

Through the LAA occluder with this structure, it is only necessary to inject the sealed seed source 301 into the balloon 701 through the catheter, so that after the LAA occluder is implanted, the myocardial cells near the ostium of the LAA 101 are radiated by the sealed seed source 301 and the myocardial cells become necrotic, thereby forming an annular isolation band to block the electrical signal conduction between the ostium of the LAA 101 and the left atrium to achieve a good electrical isolation effect. The operation mode is simple and easy to operate.

Each feature of the above-described embodiments can be combined in any combination, and in order to make the description concise, not all the possible combinations of each feature in the above-described embodiments are described. However, as long as there is no contradiction between the combinations of these features, they should be considered as the scope of the embodiments.

The above-described embodiments express only a few possible implementations, which are described in greater detail but are not to be construed as limiting the scope of the embodiments. It will be appreciated by those of ordinary skill in the art that numerous variations and modifications may be made to the embodiments without departing from the concept of the embodiments.

The invention claimed is:

1. A left atrial appendage (LAA) occluder, comprising a sealing portion and a fixing portion connected to the sealing portion,
wherein the LAA occluder further comprises one or more sealed seed sources encapsulated with radioactive particles,
wherein the sealing portion comprises a sealing disc and a balloon having an open end, a proximal end of the sealing disc is provided with a hollow proximal connector, the balloon is located inside the sealing disc, and the open end is sleeved at a distal end of the hollow proximal connector;
wherein the sealed seed sources are arranged on the sealing portion and/or the fixing portion and used to form an annular isolation band on an inner wall of an LAA after the radioactive particles are released, and the annular isolation band is used to block the electrical signal conduction between the LAA and a left atrium.

2. The LAA occluder according to claim 1, wherein the sealing portion or the fixing portion is provided with at least one flow blocking film on which the sealed seed sources are fixed.

3. The LAA occluder according to claim 2, wherein the sealed seed sources are evenly distributed near an edge of the flow blocking film.

4. The LAA occluder according to claim 1, wherein the fixing portion comprises a plurality of supporting rods or woven wires, which are provided with the sealed seed sources respectively.

5. The LAA occluder according to claim 4, wherein at least one supporting rod is provided with a hole-groove structure in which the sealed seed sources are fixedly placed.

6. The LAA occluder according to claim 5, wherein the sealed seed sources are arranged at a proximal end of the fixing portion.

7. The LAA occluder according to claim 1, wherein the sealed seed sources are evenly distributed in a circumferential direction of the sealing portion or the fixing portion.

8. The LAA occluder according to claim 7, wherein vertical distances from the various sealed seed sources on the sealing portion or the fixing portion to a central axis of the LAA occluder are equal.

9. The LAA occluder according to claim 1, wherein the sealed seed source is capable of being injected into the balloon through a catheter when the LAA occluder is unfolded, wherein the catheter is removably connected to the proximal connector.

10. The LAA occluder according to claim 9, wherein the proximal connector has a threaded hole, and the threaded hole is configured for a threaded connection with the catheter.

11. The LAA occluder according to claim 1, wherein the sealing disc further comprises a proximal disc surface and a distal disc surface, wherein a flow blocking membrane is arranged on the sealing disc, and the flow blocking membrane is located between the balloon and the distal disc surface.

* * * * *